(12) United States Patent
Firkins et al.

(10) Patent No.: US 8,414,614 B2
(45) Date of Patent: Apr. 9, 2013

(54) IMPLANT KIT FOR SUPPORTING A SPINAL COLUMN

(75) Inventors: Paul Firkins, Neuchatel (CH); Marc Sanders, Hengelo (NL)

(73) Assignee: DePuy International Ltd (GB)

( * ) Notice: Subject to any disclaimer, the term of this patent is extended or adjusted under 35 U.S.C. 154(b) by 0 days.

(21) Appl. No.: 12/090,806

(22) PCT Filed: Oct. 20, 2006

(86) PCT No.: PCT/GB2006/003907
§ 371 (c)(1),
(2), (4) Date: Aug. 4, 2008

(87) PCT Pub. No.: WO2007/045892
PCT Pub. Date: Apr. 26, 2007

(65) Prior Publication Data
US 2009/0222042 A1 Sep. 3, 2009

(30) Foreign Application Priority Data

Oct. 22, 2005 (GB) .................................. 0521582.7

(51) Int. Cl.
*A61B 17/70* (2006.01)
(52) U.S. Cl.
USPC .......................................................... 606/246
(58) Field of Classification Search .................. 606/246,
606/255, 257, 258, 259, 260, 261, 262, 264,
606/265, 270, 273, 278, 301, 305, 308, 78,
606/90, 105; 403/362; 411/393
See application file for complete search history.

(56) References Cited

U.S. PATENT DOCUMENTS

| | | | |
|---|---|---|---|
| 2,669,896 A | 2/1954 | Clough |
| 2,952,285 A | 9/1960 | Roosli |
| 3,604,487 A | 9/1971 | Gilbert |
| 3,786,806 A | 1/1974 | Johnson |
| 3,915,160 A | 10/1975 | Lode |
| 4,289,123 A | 9/1981 | Dunn |
| 4,363,250 A | 12/1982 | Suga |
| 4,592,933 A | 6/1986 | Meyerson |
| 4,611,582 A | 9/1986 | Duff |

(Continued)

FOREIGN PATENT DOCUMENTS

| DE | 3923996 | 8/1993 |
|---|---|---|
| DE | 199218381 | 4/1994 |

(Continued)

OTHER PUBLICATIONS

Advanced Energy, Industrial Processes: "Infrared (IR) Heating," "Microwave Heating," Radio Frequency and "Catalytic Heating," (2003).

(Continued)

*Primary Examiner* — Eduardo C Robert
*Assistant Examiner* — David Comstock

(57) ABSTRACT

An implant kit for supporting a spinal column comprises at least first and second support elements (8, 10, 12) for fixation to vertebrae of a spinal column, extending generally along the spinal column between spaced apart vertebrae. The kit includes a plurality of fixation devices for (i) fixing the support elements to one another in an end-to-end arrangement and (ii) fixing the support elements to the vertebrae. At least the first support element is formed from a material which exhibits shape memory properties.

20 Claims, 4 Drawing Sheets

U.S. PATENT DOCUMENTS

| | | |
|---|---|---|
| 4,697,582 A | 10/1987 | William |
| 4,733,657 A | 3/1988 | Kluger |
| 4,743,260 A | 5/1988 | Burton |
| 4,887,596 A | 12/1989 | Sherman |
| 4,957,495 A | 9/1990 | Kluger |
| 4,987,892 A | 1/1991 | Krag |
| 5,005,562 A | 4/1991 | Cotrel |
| 5,042,982 A | 8/1991 | Harms |
| 5,067,955 A | 11/1991 | Cotrel |
| 5,092,866 A | 3/1992 | Breard |
| 5,102,412 A | 4/1992 | Rogozinski |
| 5,120,171 A | 6/1992 | Lasner |
| 5,129,388 A | 7/1992 | Vignaud |
| 5,129,900 A | 7/1992 | Asher |
| 5,133,716 A | 7/1992 | Plaza |
| 5,176,678 A | 1/1993 | Tsou |
| 5,176,680 A | 1/1993 | Vignaud |
| 5,181,917 A | 1/1993 | Rogozinski |
| 5,190,543 A | 3/1993 | Schlapfer |
| 5,207,678 A | 5/1993 | Harms |
| 5,219,349 A | 6/1993 | Krag |
| 5,226,766 A | 7/1993 | Lasner |
| 5,263,939 A | 11/1993 | Wortrich |
| 5,282,801 A | 2/1994 | Sherman |
| 5,282,863 A | 2/1994 | Burton |
| 5,290,289 A | 3/1994 | Sanders |
| 5,312,404 A | 5/1994 | Asher |
| 5,330,473 A | 7/1994 | Howland |
| 5,360,431 A | 11/1994 | Puno |
| 5,385,565 A | 1/1995 | Ray |
| 5,387,212 A | 2/1995 | Yuan |
| 5,387,213 A | 2/1995 | Breard |
| 5,391,168 A | 2/1995 | Sanders |
| 5,413,576 A | 5/1995 | Rivard |
| 5,415,661 A | 5/1995 | Holmes |
| 5,437,669 A | 8/1995 | Yuan et al. |
| 5,437,673 A | 8/1995 | Baust et al. |
| 5,445,140 A | 8/1995 | Tovey |
| 5,466,238 A | 11/1995 | Lin |
| 5,468,241 A | 11/1995 | Metz Stavenhagen |
| 5,487,742 A | 1/1996 | Cotrel |
| 5,487,744 A | 1/1996 | Howland |
| 5,499,983 A | 3/1996 | Hughes |
| 5,501,684 A | 3/1996 | Schlapfer |
| 5,520,689 A | 5/1996 | Schlapfer |
| 5,536,127 A | 7/1996 | Pennig |
| 5,536,268 A | 7/1996 | Griss |
| 5,540,688 A | 7/1996 | Navas |
| 5,540,689 A | 7/1996 | Sanders |
| 5,545,165 A | 8/1996 | Biedermann |
| 5,549,552 A | 8/1996 | Peters |
| 5,549,608 A | 8/1996 | Errico |
| 5,586,983 A | 12/1996 | Sanders |
| 5,591,166 A | 1/1997 | Bernhardt |
| 5,593,407 A | 1/1997 | Reis |
| 5,593,408 A | 1/1997 | Gayet |
| 5,597,378 A | 1/1997 | Jervis |
| 5,601,552 A | 2/1997 | Cotrel |
| 5,626,581 A | 5/1997 | Staehlin |
| 5,630,816 A | 5/1997 | Kambin |
| 5,645,520 A | 7/1997 | Nakamura |
| 5,649,931 A | 7/1997 | Bryant |
| 5,651,789 A | 7/1997 | Cotrel |
| 5,658,286 A | 8/1997 | Sava |
| 5,667,513 A | 9/1997 | Torrie |
| 5,672,175 A | 9/1997 | Martin |
| 5,672,176 A | 9/1997 | Biedermann |
| 5,702,452 A | 12/1997 | Argenson |
| 5,725,527 A | 3/1998 | Biedermann |
| 5,738,685 A | 4/1998 | Halm |
| 5,743,907 A | 4/1998 | Asher |
| 5,743,911 A | 4/1998 | Cotrel |
| 5,766,004 A | 6/1998 | Besselink |
| 5,797,911 A | 8/1998 | Sherman |
| 5,830,179 A | 11/1998 | Mikus |
| 5,833,707 A | 11/1998 | McIntyre |
| 5,879,350 A | 3/1999 | Sherman |
| 5,885,285 A | 3/1999 | Simonson |
| 5,899,903 A | 5/1999 | Cotrel |
| RE36,221 E | 6/1999 | Breard |
| 5,910,141 A | 6/1999 | Morrison |
| 5,910,142 A | 6/1999 | Tatar |
| 5,919,158 A | 7/1999 | Saperstein |
| 5,947,965 A | 9/1999 | Bryan |
| 5,947,966 A | 9/1999 | Drewry |
| 5,951,555 A | 9/1999 | Rehak |
| 5,961,515 A | 10/1999 | Taylor |
| 5,964,760 A | 10/1999 | Richelsoph |
| 5,964,770 A | 10/1999 | Flomenblit |
| 5,989,250 A | 11/1999 | Wagner |
| 5,989,254 A | 11/1999 | Katz |
| 5,997,580 A | 12/1999 | Mastrorio |
| 6,050,997 A | 4/2000 | Mullane |
| 6,063,090 A | 5/2000 | Schlapfer |
| 6,071,250 A | 6/2000 | Douglas |
| 6,074,391 A | 6/2000 | Metz Stavenhagen |
| 6,077,262 A | 6/2000 | Schlapfer |
| 6,090,110 A | 7/2000 | Metz-Stavenhagen |
| 6,090,113 A | 7/2000 | Le Couedic |
| 6,102,912 A | 8/2000 | Cazin |
| 6,106,527 A | 8/2000 | Wu |
| 6,110,172 A | 8/2000 | Jackson |
| 6,127,597 A | 10/2000 | Beyar |
| 6,139,548 A | 10/2000 | Errico |
| 6,139,549 A | 10/2000 | Keller |
| 6,146,383 A | 11/2000 | Studer |
| 6,183,472 B1 | 2/2001 | Lutz |
| 6,200,317 B1 | 3/2001 | Aalsma |
| 6,204,060 B1 | 3/2001 | Mehtali |
| 6,214,006 B1 | 4/2001 | Metz Stavenhagen |
| 6,214,730 B1 | 4/2001 | Cooney, III |
| 6,235,028 B1 | 5/2001 | Brumfield |
| 6,238,491 B1 | 5/2001 | Davidson |
| 6,241,730 B1 | 6/2001 | Alby |
| 6,254,602 B1 | 7/2001 | Justis |
| 6,261,287 B1 | 7/2001 | Metz Stavenhagen |
| 6,261,288 B1 | 7/2001 | Jackson |
| 6,267,764 B1 | 7/2001 | Elberg |
| 6,273,914 B1 | 8/2001 | Papas |
| 6,280,442 B1 | 8/2001 | Barker |
| 6,280,443 B1 | 8/2001 | Gu |
| 6,293,949 B1 | 9/2001 | Justis |
| 6,299,216 B1 | 10/2001 | Thompson |
| 6,302,888 B1 | 10/2001 | Mellinger |
| 6,306,141 B1 | 10/2001 | Jervis |
| 6,309,389 B1 | 10/2001 | Baccelli |
| 6,309,391 B1 | 10/2001 | Crandall |
| 6,325,805 B1 | 12/2001 | Ogilvie |
| 6,328,741 B1 | 12/2001 | Richelsoph |
| 6,361,637 B2 | 3/2002 | Martin |
| 6,368,321 B1 | 4/2002 | Jackson |
| 6,379,357 B1 | 4/2002 | Bernstein |
| 6,389,710 B1 | 5/2002 | Chou |
| 6,402,752 B2 | 6/2002 | Schäffler-Wachter |
| 6,423,065 B2 | 7/2002 | Ferree |
| 6,440,133 B1 | 8/2002 | Beale |
| 6,440,137 B1 | 8/2002 | Horvath |
| 6,443,953 B1 | 9/2002 | Perra |
| 6,447,478 B1 | 9/2002 | Maynard |
| 6,471,716 B1 | 10/2002 | Pecukonis |
| 6,478,798 B1 | 11/2002 | Howland |
| 6,485,491 B1 | 11/2002 | Farris |
| 6,485,492 B1 | 11/2002 | Halm |
| 6,517,533 B1 | 2/2003 | Swaminathan |
| 6,520,962 B1 | 2/2003 | Taylor |
| 6,537,276 B2 | 3/2003 | Metz Stavenhagen |
| 6,540,748 B2 | 4/2003 | Lombardo |
| 6,540,749 B2 | 4/2003 | Schäfer |
| 6,551,320 B2 | 4/2003 | Lieberman |
| 6,554,834 B1 | 4/2003 | Crozet |
| 6,565,567 B1 | 5/2003 | Haider |
| 6,597,279 B1 | 7/2003 | Haraguchi |
| 6,616,669 B2 | 9/2003 | Ogilvie |
| 6,623,485 B2 | 9/2003 | Doubler |
| 6,648,888 B1 | 11/2003 | Shluzas |
| 6,652,526 B1 | 11/2003 | Arafiles |
| 6,660,006 B2 | 12/2003 | Markworth |

| | | |
|---|---|---|
| 6,689,137 B2 | 2/2004 | Reed |
| 6,692,500 B2 | 2/2004 | Reed |
| 6,695,843 B2 | 2/2004 | Biedermann |
| 6,706,044 B2 | 3/2004 | Kuslich |
| 6,716,214 B1 | 4/2004 | Jackson |
| 6,730,087 B1 | 5/2004 | Butsch |
| 6,733,502 B2 | 5/2004 | Altarac |
| 6,733,531 B1 | 5/2004 | Trieu |
| 6,743,231 B1 | 6/2004 | Gray |
| 6,749,613 B1 | 6/2004 | Conchy |
| 6,755,829 B1 | 6/2004 | Bono |
| 6,761,719 B2 | 7/2004 | Justis |
| 6,783,527 B2 | 8/2004 | Drewry |
| 6,786,984 B1 | 9/2004 | Hanada |
| 6,800,078 B2 | 10/2004 | Reed |
| 6,800,079 B2 | 10/2004 | Reed |
| 6,800,778 B1 | 10/2004 | Aoki |
| 6,802,844 B2 | 10/2004 | Ferree |
| 6,837,889 B2 | 1/2005 | Shluzas |
| 6,872,208 B1 | 3/2005 | McBride |
| 6,881,220 B2 | 4/2005 | Edwin |
| 6,887,241 B1 | 5/2005 | McBride |
| 6,964,666 B2 | 11/2005 | Jackson |
| 6,984,242 B2 | 1/2006 | Campbell |
| 6,986,771 B2 | 1/2006 | Paul |
| 6,989,011 B2 * | 1/2006 | Paul et al. .................. 606/250 |
| 7,010,866 B1 | 3/2006 | Lin |
| 7,044,966 B2 | 5/2006 | Svanidze |
| 7,044,982 B2 | 5/2006 | Milbocker |
| 7,063,706 B2 | 6/2006 | Wittenstein |
| 7,066,938 B2 | 6/2006 | Slivka |
| 7,094,237 B2 | 8/2006 | Gradel |
| 7,104,993 B2 | 9/2006 | Baynham |
| 7,125,410 B2 | 10/2006 | Freudiger |
| 7,128,743 B2 | 10/2006 | Metz Stavenhagen |
| 7,128,758 B2 | 10/2006 | Cox |
| 7,179,261 B2 | 2/2007 | Sicvol |
| 7,207,986 B2 | 4/2007 | Abboud |
| 7,267,687 B2 | 9/2007 | McGuckin, Jr. |
| 7,322,979 B2 | 1/2008 | Crandall |
| 7,335,200 B2 | 2/2008 | Carli |
| 7,377,923 B2 | 5/2008 | Purcell |
| 7,381,625 B2 | 6/2008 | Xi |
| 7,429,042 B2 | 9/2008 | Ban |
| 7,442,192 B2 | 10/2008 | Knowlton |
| 7,455,685 B2 | 11/2008 | Justis |
| 7,459,042 B2 | 12/2008 | Parker |
| 7,465,306 B2 | 12/2008 | Pond, Jr. |
| 7,473,267 B2 | 1/2009 | Nguyen |
| 7,481,827 B2 | 1/2009 | Ryan |
| 7,491,218 B2 | 2/2009 | Landry |
| 7,494,488 B2 | 2/2009 | Weber |
| 7,507,248 B2 | 3/2009 | Beaurain |
| 7,559,942 B2 | 7/2009 | Paul |
| 7,588,575 B2 | 9/2009 | Colleran |
| 7,604,653 B2 | 10/2009 | Kitchen |
| 7,621,912 B2 | 11/2009 | Harms |
| 7,632,292 B2 | 12/2009 | Sengupta |
| 7,635,380 B2 | 12/2009 | Zucherman |
| 7,641,673 B2 | 1/2010 | Le Couedic |
| 7,658,739 B2 | 2/2010 | Shluzas |
| 7,666,189 B2 | 2/2010 | Gerber |
| 7,691,145 B2 | 4/2010 | Reiley |
| 7,699,872 B2 | 4/2010 | Farris |
| 7,749,258 B2 | 7/2010 | Biedermann |
| 7,763,048 B2 | 7/2010 | Fortin |
| 7,763,049 B2 | 7/2010 | Roychowdhury |
| 7,766,944 B2 | 8/2010 | Metz-Stavenhagen |
| 7,776,071 B2 | 8/2010 | Fortin |
| 7,780,706 B2 | 8/2010 | Marino |
| 7,789,897 B2 | 9/2010 | Sanders |
| 7,794,476 B2 | 9/2010 | Wisnewski |
| 7,927,353 B2 | 4/2011 | Taylor |
| 7,976,568 B2 | 7/2011 | Cheung |
| 7,988,713 B2 | 8/2011 | Metz-Stavenhagen |
| 8,002,806 B2 | 8/2011 | Justis |
| 8,007,520 B2 | 8/2011 | Metz-Stavenhagen |
| 8,021,389 B2 | 9/2011 | Molz, IV |
| 8,048,127 B2 | 11/2011 | Moulin |
| 8,048,133 B2 | 11/2011 | Biedermann |
| 8,075,591 B2 | 12/2011 | Ludwig |
| 2001/0020169 A1 | 9/2001 | Metz Stavenhagen |
| 2002/0032442 A1 | 3/2002 | Altarac |
| 2002/0035366 A1 | 3/2002 | Walder |
| 2002/0082599 A1 | 6/2002 | Crandall |
| 2002/0133155 A1 | 9/2002 | Ferree |
| 2002/0138077 A1 | 9/2002 | Ferree |
| 2002/0143327 A1 | 10/2002 | Shluzas |
| 2002/0143341 A1 | 10/2002 | Biedermann |
| 2002/0169449 A1 | 11/2002 | Kuslich |
| 2002/0173789 A1 | 11/2002 | Howland |
| 2003/0004512 A1 | 1/2003 | Farris |
| 2003/0023240 A1 | 1/2003 | Amrein |
| 2003/0073995 A1 | 4/2003 | Reed |
| 2003/0083657 A1 | 5/2003 | Drewry |
| 2003/0088248 A1 | 5/2003 | Reed |
| 2003/0100896 A1 | 5/2003 | Biedermann |
| 2003/0105460 A1 | 6/2003 | Crandall |
| 2003/0109880 A1 | 6/2003 | Shirado |
| 2003/0114853 A1 | 6/2003 | Burgess |
| 2003/0171749 A1 | 9/2003 | Le Couedic |
| 2003/0176861 A1 | 9/2003 | Reed |
| 2003/0191470 A1 | 10/2003 | Ritland |
| 2003/0203488 A1 | 10/2003 | Mehtali |
| 2003/0220642 A1 | 11/2003 | Freudiger |
| 2003/0220643 A1 | 11/2003 | Ferree |
| 2004/0002708 A1 | 1/2004 | Ritland |
| 2004/0049189 A1 | 3/2004 | Le Couedic |
| 2004/0049190 A1 | 3/2004 | Biedermann |
| 2004/0073215 A1 | 4/2004 | Carli |
| 2004/0106921 A1 | 6/2004 | Cheung |
| 2004/0158258 A1 | 8/2004 | Bonati |
| 2004/0162558 A1 | 8/2004 | Hegde |
| 2004/0172020 A1 | 9/2004 | Beaurain |
| 2004/0172025 A1 | 9/2004 | Drewry |
| 2004/0181224 A1 | 9/2004 | Biedermann |
| 2004/0186472 A1 | 9/2004 | Lewis |
| 2004/0186473 A1 | 9/2004 | Cournoyer |
| 2004/0204711 A1 | 10/2004 | Jackson |
| 2004/0215191 A1 | 10/2004 | Kitchen |
| 2004/0225289 A1 | 11/2004 | Biedermann |
| 2004/0236330 A1 | 11/2004 | Purcell |
| 2004/0254577 A1 | 12/2004 | Delecrin |
| 2004/0260285 A1 | 12/2004 | Steib |
| 2004/0267260 A1 | 12/2004 | Mack |
| 2004/0267275 A1 | 12/2004 | Cournoyer |
| 2005/0010216 A1 | 1/2005 | Gradel |
| 2005/0010233 A1 | 1/2005 | Wittenstein |
| 2005/0010778 A1 | 1/2005 | Walmsley |
| 2005/0033291 A1 | 2/2005 | Ebara |
| 2005/0033295 A1 | 2/2005 | Wisnewski |
| 2005/0038430 A1 | 2/2005 | McKinley |
| 2005/0065514 A1 | 3/2005 | Studer |
| 2005/0065515 A1 | 3/2005 | Jahng |
| 2005/0065516 A1 | 3/2005 | Jahng |
| 2005/0070899 A1 | 3/2005 | Doubler |
| 2005/0070917 A1 | 3/2005 | Justis |
| 2005/0085815 A1 | 4/2005 | Harms |
| 2005/0107788 A1 | 5/2005 | Beaurain |
| 2005/0124991 A1 | 6/2005 | Jahng |
| 2005/0131408 A1 | 6/2005 | Sicvol |
| 2005/0131422 A1 | 6/2005 | Anderson |
| 2005/0149020 A1 | 7/2005 | Jahng |
| 2005/0154390 A1 | 7/2005 | Biedermann |
| 2005/0159650 A1 | 7/2005 | Raymond |
| 2005/0171538 A1 | 8/2005 | Sgier |
| 2005/0177157 A1 | 8/2005 | Jahng |
| 2005/0192573 A1 | 9/2005 | Abdelgany |
| 2005/0192589 A1 | 9/2005 | Raymond |
| 2005/0203511 A1 | 9/2005 | Wilson MacDonald |
| 2005/0203518 A1 | 9/2005 | Biedermann |
| 2005/0222570 A1 | 10/2005 | Jackson |
| 2005/0222683 A1 | 10/2005 | Berry |
| 2005/0228376 A1 | 10/2005 | Boomer |
| 2005/0228378 A1 | 10/2005 | Kalfas |
| 2005/0228379 A1 | 10/2005 | Jackson |
| 2005/0240265 A1 | 10/2005 | Kuiper |
| 2005/0245928 A1 | 11/2005 | Colleran |

| Publication No. | Date | Name |
|---|---|---|
| 2005/0261687 A1 | 11/2005 | Garamszegi |
| 2005/0261770 A1 | 11/2005 | Kuiper |
| 2005/0277932 A1 | 12/2005 | Farris |
| 2005/0283244 A1 | 12/2005 | Gordon |
| 2005/0288668 A1 | 12/2005 | Brinkhaus |
| 2006/0009767 A1 | 1/2006 | Kiester |
| 2006/0015527 A1 | 1/2006 | Dingle |
| 2006/0025769 A1 | 2/2006 | Dick |
| 2006/0036255 A1 | 2/2006 | Pond |
| 2006/0064090 A1 | 3/2006 | Park |
| 2006/0111715 A1 | 5/2006 | Jackson |
| 2006/0149228 A1 | 7/2006 | Schlapfer |
| 2006/0149236 A1 | 7/2006 | Barry |
| 2006/0149237 A1 | 7/2006 | Markworth |
| 2006/0149240 A1 | 7/2006 | Jackson |
| 2006/0155277 A1 | 7/2006 | Metz Stavenhagen |
| 2006/0161152 A1 | 7/2006 | Ensign |
| 2006/0173454 A1 | 8/2006 | Spitler |
| 2006/0184171 A1 | 8/2006 | Biedermann |
| 2006/0195092 A1 | 8/2006 | Barry |
| 2006/0200129 A1 | 9/2006 | Denti |
| 2006/0200131 A1 | 9/2006 | Chao |
| 2006/0200132 A1 | 9/2006 | Chao |
| 2006/0206114 A1 | 9/2006 | Ensign |
| 2006/0217735 A1 | 9/2006 | MacDonald |
| 2006/0229607 A1* | 10/2006 | Brumfield ........................ 606/61 |
| 2006/0229614 A1 | 10/2006 | Foley |
| 2006/0229615 A1 | 10/2006 | Abdou |
| 2006/0235389 A1 | 10/2006 | Albert |
| 2006/0240533 A1 | 10/2006 | Sengupta |
| 2006/0264935 A1 | 11/2006 | White |
| 2006/0264937 A1 | 11/2006 | White |
| 2006/0271193 A1 | 11/2006 | Hartmann |
| 2006/0282073 A1 | 12/2006 | Simanovsky |
| 2007/0016201 A1 | 1/2007 | Freudiger |
| 2007/0049937 A1 | 3/2007 | Matthis |
| 2007/0055240 A1 | 3/2007 | Matthis |
| 2007/0090238 A1 | 4/2007 | Justis |
| 2007/0161990 A1 | 7/2007 | Hillyard |
| 2007/0161994 A1 | 7/2007 | Lowery |
| 2007/0162007 A1 | 7/2007 | Shoham |
| 2007/0162009 A1 | 7/2007 | Chao |
| 2007/0162010 A1 | 7/2007 | Chao |
| 2007/0173800 A1 | 7/2007 | Sanders |
| 2007/0173828 A1 | 7/2007 | Firkins |
| 2007/0179501 A1 | 8/2007 | Firkins |
| 2007/0191831 A1 | 8/2007 | Sanders |
| 2007/0191841 A1 | 8/2007 | Justis |
| 2007/0191842 A1 | 8/2007 | Molz |
| 2007/0198088 A1 | 8/2007 | Biedermann |
| 2007/0213721 A1 | 9/2007 | Markworth |
| 2007/0213723 A1 | 9/2007 | Markworth |
| 2007/0239154 A1 | 10/2007 | Shaolian |
| 2007/0270843 A1 | 11/2007 | Matthis |
| 2007/0288013 A1 | 12/2007 | Sanders |
| 2008/0021456 A1 | 1/2008 | Gupta |
| 2008/0027436 A1 | 1/2008 | Cournoyer |
| 2008/0058805 A1 | 3/2008 | Stuart |
| 2008/0071373 A1 | 3/2008 | Molz |
| 2008/0114404 A1 | 5/2008 | Matthis |
| 2008/0195159 A1 | 8/2008 | Kloss |
| 2008/0234756 A1 | 9/2008 | Sutcliffe |
| 2008/0243189 A1 | 10/2008 | Purcell |
| 2008/0269805 A1 | 10/2008 | Dekutoski |
| 2009/0048632 A1 | 2/2009 | Firkins |
| 2009/0182381 A1 | 7/2009 | Beaurain |
| 2009/0198280 A1 | 8/2009 | Spratt |
| 2009/0222042 A1 | 9/2009 | Firkins |
| 2010/0010547 A1 | 1/2010 | Beaurain |
| 2010/0042156 A1 | 2/2010 | Harms |
| 2010/0063548 A1 | 3/2010 | Wang |
| 2010/0114169 A1 | 5/2010 | Le Couedic |
| 2010/0114173 A1 | 5/2010 | Le Couedic |
| 2010/0249848 A1 | 9/2010 | Wisnewski |

FOREIGN PATENT DOCUMENTS

| Country | Number | Date |
|---|---|---|
| DE | 199314297 | 5/1994 |
| DE | 199402695 | 5/1994 |
| DE | 4107480 | 9/1994 |
| DE | 4330837 | 3/1995 |
| DE | 10005385 | 8/2001 |
| DE | 10005386 | 8/2001 |
| EP | 134622 | 10/1986 |
| EP | 470660 | 2/1992 |
| EP | 441729 | 1/1994 |
| EP | 592266 | 4/1994 |
| EP | 328883 | 7/1994 |
| EP | 487895 | 1/1995 |
| EP | 470660 | 7/1995 |
| EP | 572790 | 2/1996 |
| EP | 558883 | 7/1997 |
| EP | 811357 | 12/1997 |
| EP | 846444 | 6/1998 |
| EP | 669109 | 5/1999 |
| EP | 381588 | 5/2000 |
| EP | 784693 | 10/2001 |
| EP | 1295566 | 3/2003 |
| EP | 951246 | 5/2003 |
| EP | 880344 | 8/2003 |
| EP | 1090595 | 12/2003 |
| EP | 885598 | 4/2005 |
| EP | 1364622 | 7/2005 |
| FR | 2624720 | 6/1989 |
| FR | 2759894 | 8/1998 |
| FR | 2786088 | 5/2000 |
| FR | 2806615 | 9/2001 |
| FR | 2813782 | 3/2002 |
| FR | 2839880 | 11/2003 |
| WO | 9002527 | 3/1990 |
| WO | 9822033 | 5/1998 |
| WO | 9900065 | 1/1999 |
| WO | 9944527 | 9/1999 |
| WO | 0145576 | 6/2001 |
| WO | 0157801 | 12/2001 |
| WO | 0191656 | 12/2001 |
| WO | 0207622 | 1/2002 |
| WO | 0191656 | 5/2002 |
| WO | 0234310 | 5/2002 |
| WO | 02102259 | 12/2002 |
| WO | 03007828 | 1/2003 |
| WO | 0234310 | 2/2003 |
| WO | 03049629 | 6/2003 |
| WO | 03032863 | 12/2003 |
| WO | 2004034916 | 4/2004 |
| WO | 2004041100 | 5/2004 |
| WO | 2004019755 | 7/2004 |
| WO | 2005044123 | 5/2005 |
| WO | 2005044117 | 8/2005 |
| WO | 2006101898 | 9/2006 |
| WO | 2007041265 | 4/2007 |
| WO | 2007045892 | 4/2007 |
| WO | 2007045899 | 4/2007 |
| WO | 2006130179 | 10/2007 |
| WO | 2008000944 | 5/2008 |

OTHER PUBLICATIONS

Andreasen G (1980) A clinical trial of alignment of teeth using 0.019-inch thermal nitinol wire with transitional temperature range between 31° C. and 45° C. Am) Orthod 78:528-537.

Asher MA, Burton DC. Adolescent idiopathic scoliosis: natural history and long term treatment effects. Scoliosis 2006; 1:2.

Betz RR, Kim J, D'Andrea LP, et al. An innovative technique of vertebral body stapling for the treatment of patients with adolescent idiopathic scoliosis: a feasibility, safety, and utility study. Spine 2003;28(suppl):255-65.

Bischoff R, Bennett JT, Stuecker R, et al. The use of TexasScottish-Rite instrumentation in idiopathic scoliosis. A preliminary report. Spine 1993 18:2452-2456.

Boos N, Webb JK. Pedicle screw fixation in spinal disorders : a European view. Eur Spine) 1997;6:2-18.

Braun et al., "Mechanical modulation of vertebral growth in the fusion less treatment of progressive scoliosis in an experimental model"; Spine; May 20, 2006; 31(12):1314-20.

Braun JT, Hines JL, Akyuz E Relative versus absolute modulation of growth in the fusionless treatment of experimental scoliosis. Spine 2006, 15;31:1776-82.

Braun JT, Ogilvie JW, Akyuz E, et al. Fusionless scoliosis correction using a shape memory alloy staple in the anterior thoracic spine of the immature goat. Spine 2004;29: 1980-9.

Bridwell KH. Surgical treatment of idiopathic adolescent scoliosis. Spine 1999;24:2607-16.

Brymill Cryogenic Systems, "CRY-AC & CRY-AC-3," retrieved online at: http://www.brymill.com/catalog_1_cryac.htm (2010).

Chemtronics, Technical Data Sheet, "Freez-It Freeze Spray," TDS#1550E.

Cotrel Y, Dubousset, Guillaumat M. New universal instrumentation in spinal surgery. Clin Orthop 1988;227: 10-23.

Cryosurgery, Inc, "Verruca-Freeze is a convenient and effective cryosurgical system for the treatment of benign skin lesions," retrieved online at: http://www.cryosurgeryinc.com/cryo/cryosurgeryweb.nsf/0/9C997EB18781696E85256DCB005627D2?opendocument (2005).

Cryosurgery, Inc., "Comparison of Cryosurgical Systems,".

GHS Medical, "Our Light Coagulator Product Family," retrieved online at: http://www/ghs-medical.com/geraeteha02.htm (2005).

Goshi K, Boachie-Adjei 0, Moore C, Nishiyama M. Thoracic scoliosis fusion in adolescent and adult idiopathic scoliosis using posterior translational corrective techniques (Isola): is maximum correction of the thoracic curve detrimental to the unfused lumbar curve? Spine J 2004; 4:192-201.

Halm HF, Niemeyer T, Link TM, et al. Segmental pedicle screw instrumentation in idiopathic thoracolumbar and lumbar scoliosis. Eur Spine) 2000; 9:192-7.

Hamill CI, Lenke IG, Bridwell KH, et al. The use of pedicle screw fixation to improve correction in the lumbar s'pine of patients with idiopathic scoliosis. Is it warranted? Spine 1996;21: 1241-9.

Harrington PRo Treatment of scoliosis: correction and internal fixation by spine instrumentation. J Bone Joint Surg Am 1962;44:591-634.

Kim YJ, Lenke LG, Kim J, et al. Comparative analysis of pedicle screw versus hybrid instrumentation in posterior spinal fusion of adolescent idiopathic scoliosis. Spine 2006;31:291-298.

Lehman RA Jr, Polly DW Jr, Kuklo TR, et al. Straight-forward versus anatomic trajectory technique of thoracic pedicle screw fixation: a biomechanical analysis. Spine 2003; 28:2058-2065.

Liljenqvist UR, Halm HF, Link TM. Pedicle screw instrumentation of the thoracic spine in idiopathic scoliosis. Spine 1997;22:2239-45.

Liu XM, Wu SI, Chan YL, et al. Surface characteristics, biocompatibility, and mechanical properties of nickel-titanium plasma-implanted with nitrogen at different implantation voltages. J Biomed Mater Res A. 2007; 82:469-78.

Lumatec "Infrared-Coagulator".

Matsumoto K, Tajima N, Kuwahara S. Correction of scoliosis with shape-memory alloy. Nippon Seikeigeka Gakkai Zasshi. Apr. 1993;67(4): 267-74.

Misenhimer GR, Peek RD, Wiltse LL, et al. Anatomic analysis of pedicle cortical and cancellous diameter as related to screw size. Spine 1989;14:367-72.

NDC, Nitinol Devices & Components, "Nitinol Technology," retrieved online at: http://www.nitinol.com/3tech.htm (2001).

Niti Smart Sheet, retrieved online at: http://www.sma.inc.com (2001).

Puttlitz et al,. A biomechanical assessment of thoracic spine stapling. Spine. Apr. 2007.

Sanders, "Preliminary investigation of shape memory alloys in the surgical correction of Scoliosis"; Spine; Sep. 15, 1993; 18(12):1640-6.

Steinmann JC, Herkowitz HN, el-Kommos H, et al. Spinal pedicle fixation: Confirmation of an image-based technique for screw placement. Spine 1993; 18:8560-61.

Suk SI, Kim W), Iee SM, Kim )H, Chung ER. Thoracic pedicle screw fixation in spinal deformities: are they really safe? Spine 2001;26:2049-57.

Suk SI, Iee CK, Kim W), et al. Segmental pedicle screw fixation in the treatment of thoracic idiopathic scoliosis. Spine 1995;20: 1399-405.

Svetlana A., Shabaloskay A. Surface corrosion and biocompatibility aspects of Nitinol as an implant material, Journal of Biomedical Materials Engineering, 2002, 12: 692109.

Szold A. Nitinol: shape-memory and super-elastic materials in surgery. *Surg Endosc*. 2006;20:1493-1496, doi: 10,1007/s00464-005-0867-1.

Takeshita K, Maruyama T, Murakami M, et al. Correction of scoliosis using segmental pedicle screw instrumentation versus hybrid constructs with hooks and screws. Stud Health Technol Inform 2006; 123:571-576.

Veldhuizen, A.G. et al., "A scoliosis correction device based on memory metal," Med. Eng. Phys., vol. 19 (2):171-179 (1997).

Wang A, Peng ), Zhang X, et al. Experimental study of recovery force of surface-modified TiNi memory alloy rod Sheng Wu Yi Xue Gong Cheng Xue Za Zhi. 2006;23:774-7.

Wever et al., "Scoliosis correction with shape-memory metal: results of an experimental study"; .Eur Spine J.; Apr. 2002; 11(2):100-6. Epub Nov. 14, 2001.

Wu S, Liu X, Chan YL,et al. Nickel release behavior, cytocompatibility, and superelasticity of oxidized porous single-phase NiTLJ Biomed Mater Res A. 2007; 81:948-55.

Yeung KW, Poon RW, Chu PK, et al. Surface mechanical properties, corrosion resistance, and cytocompatibility of nitrogen plasma-implanted nickel-titanium alloys: A comparative study with commonly used medical grade materials.) Biomed Mater Res A. 2007; 82:403-14.

Zdeblick 'Anterior Spinal Fixation after Lumbar Corpectomy' A Study in Dogs, Journal of Bone and Joint Surgery, vol. 73-A, #4, Apr. 1991, p. 527-534.

Zindrick MR, Knight GW, Satori MJ, et al. Pedicle morphology of the immature thoracolumbar spine. Spine 2000;25:2726-35.

European Search Report for GB0521589 dated Aug. 28, 2006.

European Search Report for GB07250128.1 dated Apr. 25, 2007.

Wiltse, Leon L. et al., "History of Pedicle Screw Fixation of the Spine," Spine, State of the Art Reviews, vol. 6(1):1-10 (1992).

\* cited by examiner

IMPLANT KIT FOR SUPPORTING A SPINAL COLUMN

This invention relates to an implant kit for supporting a spinal column.

EP-A-470660 discloses apparatus for correcting the shape of a spinal column. The apparatus includes a rod which is formed from a nickel-titanium alloy which has been treated so that it exhibits shape memory properties, in bending or in torsion or both. Articles formed from shape memory alloys can exhibit shape memory properties associated with transformations between martensite and austenite phases of the alloys. These properties include thermally induced changes in configuration in which an article is first deformed from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase. The transformation from austenite to martensite on cooling begins at a temperature known as the $M_s$ temperature, and is completed at a temperature known as the $M_f$ temperature. The transformation of martensite to austenite upon heating begins at a temperature known as the $A_s$ temperature and is complete at a temperature known as the $A_f$ temperature.

The rod of the apparatus disclosed in EP-A-470660 is fastened to a patient's vertebrae while in the configuration from which it has to recover. The temperature of the rod is then increased so that it is greater than the $A_s$ temperature of the alloy. The rod then recovers towards its heat-stable configuration, applying a corrective force to the spinal column.

It can be important to select a rod having configurations both before and after recover which are suitable for the particular patient, having regard to the nature of the deformity of the spinal column which is to be corrected. Variations between patients can require variations in features such as rod length, rod curvature, and the location of curvature along the length of the rod. It is not feasible for the curvature or the length of a rod to be changed after manufacture. Accordingly, it can be necessary to supply a large inventory of rods to a surgeon in order for him to be able to optimise the fit of a rod to a particular patient.

The present invention provides an implant kit for supporting a spinal column, which comprises at least first and second support elements for fixation to vertebrae of a spinal column in which at least the first support element is formed from a material which exhibits shape memory properties.

Accordingly, in one aspect, the invention provides an implant kit for supporting a spinal column, which comprises:
 a. at least first and second support elements for fixation to vertebrae of a spinal column, extending generally along the spinal column between spaced apart vertebrae,
 b. a plurality of fixation devices for (i) fixing the support elements to one another in an end-to-end arrangement and (ii) fixing the support elements to the vertebrae,
in which at least the first support element is formed from a material which exhibits shape memory properties.

The kit of the invention has the advantage that it enables variations between patients to be accommodated with a smaller inventory than is required when a single rod is provided to extend over the length of a patient's spinal column. For example, the effective length of a spinal support assembly can be varied by changing the length of one of the support elements, preferably the second support element by cutting it, or by interchanging the second support element for another element.

The kit of the invention can be used to provide an implant which optimised to suit the requirements of an individual patient by selection of an appropriate first support element and selection of an appropriate second support element. It might be for example that the maximum correction is required in the region of the spinal column in which the first support element is to be implanted. The region of the spinal column in which the second support element is to be implanted might be relative free of deformity which is to be corrected, the second support element being used to provide support for the first support element.

The first and second support elements can differ from one another by features which include one or more of material, physical properties (for example modulus, elastic limit, etc, which might for example be introduced through different processing techniques), dimensions (especially cross-sectional size (for example diameter when the cross-sectional shape is circular, or width when it is square or rectangular)), and cross-sectional shape (for example rounded, or polygonal etc as discussed below).

One or more support elements can be formed from a shape memory alloy. The alloy can be treated so that it is implanted while in the martensite phase. The treatment of the alloy can be such that its $A_s$ and $A_f$ temperatures are between ambient temperature and body temperature (37° C.), so that the alloy is fully austenite phase at body temperature (for example by virtue of the $A_f$ temperature being less than body temperature, for example about 32° C.). This allows the surgeon to make use of the thermally initiated shape recovery properties of the alloy, in which the support element is implanted in the body in the martensite phase, which is stable at ambient temperature. On implantation, the element is exposed to body temperature which leads to the phase of the alloy transforming from martensite to austenite. The element will then tend towards a configuration from which it was transformed while in the martensite phase, applying corrective forces to a patient's vertebrae.

A support element which is formed from a shape memory alloy can apply corrective forces by virtue of the enhanced elastic properties that are available from such materials. Shape memory alloys can exhibit enhanced elastic properties compared with materials which do not exhibit martensite-austenite transformations and it is these properties that the present invention is concerned with in particular. The nature of superelastic transformations of shape memory alloys is discussed in "Engineering Aspects of Shape Memory Alloys", T W Duerig et al, on page 370, Butterworth-Heinemann (1990). Subject matter disclosed in that document is incorporated in this specification by this reference to the document. A principal transformation of shape memory alloys involves an initial increase in strain, approximately linearly with stress. This behaviour is reversible, and corresponds to conventional elastic deformation. Subsequent increases in strain are accompanied by little or no increase in stress, over a limited range of strain to the end of the "loading plateau".

The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point along which stress changes little with reducing strain. At the end of the unloading plateau, stress reduces with reducing strain. The unloading plateau stress is also defined by the inflection point on the stress/strain graph. Any residual strain after unloading to zero stress is the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys", on page 376.

A preferred way in which non-linear superelastic properties can be introduced in a shape memory alloy involves cold working the alloy by one of several deformation methods, for example, swaging, drawing, pressing, stretching or bending. The cold working step is followed by an annealing step at a temperature less than the recrystallization temperature of the alloy, for a time sufficient to cause dislocations to rearrange, combine and align themselves (so-called "recovery" processes). The resulting recovered dislocation structure should ideally be dense enough to make plastic deformation difficult, but not so dense as to prevent the martensite phase from transforming upon the application of a load, and growing in a relatively unimpeded manner.

Since many preferred superelastic alloys are thermally unstable in the temperature range in which these recovery processes occur, a second unavoidable result of this recovery heat treatment step is to age the material, that is to cause Ni-rich particles to precipitate, having the effect of enriching the matrix phase in titanium, and thus increasing the transformation temperatures (including the $A_f$ temperature). Optimum superelastic properties are only realized when using shape memory alloys above the $A_f$ temperature, though it should be noted that some indications of superelasticity are observed above the $A_s$ temperature (typically 2 to 20° C. below $A_f$). Thus a second requirement for this recovery heat treatment is that $A_f$ not be increased above the temperature at which the alloy is to be used.

Practically speaking this places upper limits on the time and temperature which can be used in the recovery heat treatment.

When it is desired only to rely on the superelastic properties of an alloy without any contribution from any thermally initiated shape memory effect, the alloy should by processed so that its $A_f$ temperature is below temperatures to which the alloy is likely to be subjected during implantation, that is preferably below about ambient temperature. For example, the $A_f$ temperature might be not more than about 20° C.

A particularly preferred kit according to the invention includes a first support element which is formed from a shape memory alloy which has been treated so that it exhibits thermally initiated shape recovery properties, and a second support element which is formed from a shape memory alloy which has been treated so that it exhibits enhanced elastic properties as discussed above. Such alloys can differ from one another in the characteristic transformation temperatures of the alloys: the alloy of the first support element should preferably have $A_s$ and $A_f$ temperatures which are between ambient temperatures to which the element is exposed prior to and during implantation and body temperature, and the alloy of the second support element should have an $A_f$ temperature which is below both ambient temperatures to which the element is exposed prior to and during implantation and body temperature.

Another preferred kit according to the invention includes a first support element which is formed from a shape memory alloy which has been treated so that it exhibits enhanced elastic properties as discussed above, and a second support element which is formed from a metal which does not exhibit shape memory properties (whether enhanced elastic properties or thermally initiated shape recovery properties). The second support element can be relied on in portions of the vertebral column to minimise relative movement between the vertebrae so that the column is stabilised in those portions. This can be with a view to promoting fusion between vertebrae. The first support element can be relied on to allow flexing of the vertebral column in portions where stabilisation is not required.

A further preferred kit according to the invention includes a first support element which is formed from a shape memory alloy which has been treated so that it exhibits thermally initiated shape recovery properties, and a second support element which is formed from a metal which does not exhibit shape memory properties (whether enhanced elastic properties or thermally initiated shape recovery properties). The second support element can be relied on in portions of the vertebral column to minimise relative movement between the vertebrae so that the column is stabilised in those portions. This can be with a view to promoting fusion between vertebrae. The first support element can be relied on to exert corrective forces on a vertebral column over time.

It is often the case that a device is to be used in a shape other than that which can be practically produced by cold working processes. For example, a straight wire can be conveniently produced by cold drawing, but a wire loop or other formed shape cannot be. In this case, it is customary to form the drawn, cold worked wire into the desired "heat stable" shape, to constrain the wire in that shape, and then to perform the above described recovery heat treatment to "shape set" the component. In this case the final annealing operation has two purposes: to adjust the superelastic properties of the alloy, and to properly set the shape of the article. The time and temperature of this heat treatment step are critical. If held too long at temperature, the material over-ages, causing the $A_f$ temperature to rise above the application temperature. If the annealing temperature is too short, or the temperature too low, the shape will be insufficiently formed, and too much of the original dislocation structure will remain to allow free martensite movement. This "forming" treatment may introduce still further cold work into the part, but that cold work is usually small compared to that introduced into the wire by drawing. Moreover, forming operations are often not uniform, and thus forming itself is not generally a convenient way to introduce cold work.

Articles of complicated shape require extensive forming and are very difficult to produce according to the above process. If the forming process causes strains which are too severe, the article will fracture as it is heated to the shape setting and recovery temperature (one is able to restrain the formed article, but cannot maintain its shape during the heating process without causing fracture). It is possible to overcome this problem by performing a series of smaller, intermediate shape setting operations which accumulate to provide the desired final shape, but unfortunately each of these shape setting operations requires sufficient annealing time to allow the material to soften, in preparation for the next. When accumulated, these heat treatments cause a cumulative ageing effect that can cause the $A_f$ temperature to rise beyond the expected service temperature (37° C., for most medical applications, for example).

It is also known that one can introduce superelasticity by solution treating and ageing, abandoning all attempts to retain cold work. Although this approach resolves the above problems, it leads to inferior superelastic properties, producing articles that are susceptible to fatigue and storage problems.

Examples of shape memory alloys which might be used in the first and possibly other support elements in the kit of the invention include nickel-titanium based alloys, especially the binary alloy which contains 50.8 at-% nickel. Suitable alloys include those which satisfy ASTM F2063-00. It will often be particularly preferred for both the first and second support elements to be formed from shape memory alloys, especially for each support element to be formed from shape memory alloys. Other metals which might be used to form support elements which do not exhibit shape memory properties include titanium and alloys thereof, for example Ti6Al4V alloys such as satisfy ASTM F136-02a or ASTM F1472-02a or both.

Materials which exhibit shape memory properties, other than alloys, can be used. For example, polymeric materials can be used. Shape memory properties can be imparted to polymeric materials by forming them in a desired ultimate shape (for example by moulding), crosslinking the material, heating the material to a temperature at which it softens, deforming the material while soft and restraining the material in the deformed configuration while it cools. The material will tend to revert towards the initial "as formed" configuration when reheated. Examples of suitable polymeric materials which can be used in this way include oligomers, homopolymers, copolymers and polymer blends which include, as monomers, l-, d- or d/l-lactide (lactic acid), glycolide (glycolic acid), ethers, ethylene, propylene and other olefins, styrene, norbornene, butadiene, poly-functional monomers such as acrylates, methacrylates, methyl acrylates, and esters such as caprolactone. The use of such polymeric materials in related applications is disclosed in WO-02/34310.

The first support element will generally be longer than the second support element. The first element will often be used to correct deformities in the thoracic region or in the lumbar region or both, where the range of motion that is available from the use of a shape memory alloy can be used to greatest advantage. The second support element can be arranged for implantation in any of the sacral, lumbar, thoracic and cervical regions. Additional support elements (for example third and optionally fourth support elements) can be included, for example so that separate support elements can be provided to extend into regions other than the region in which the first support element is provided.

The use of a material for the second support element which is not made from a shape memory alloy has the advantage that the length of the second support element can be adjusted to suit the requirements of a particular patient by cutting. Overall, the inventory that has to be maintained to enable procedures to be performed on a wide range of patients can be less than is required when the implant kit includes a single support element which is intended to extend over the full length of the patient's spinal column.

Preferably, the ratio of the length of the first support element to that of the second element is at least about 1.2, more preferably at least about 1.5, especially at least about 2.0, for example at least about 2.5.

The length of the first support element is preferably at least about 50 mm, more preferably at least about 75 mm, for example at least about 100 mm, and possibly 150 mm or more, for example up to about 300 mm. The length of the second support element is preferably at least about 30 mm, more preferably at least about 50 mm, for example at least about 80 mm, and possibly 120 mm or more. The length of the second support element might be not more than about 120 mm, preferably not more than about 100 mm, for example not more than about 80 mm, possibly not more than about 50 mm.

The angle between the end portions of the first support element can be greater than the angle between the end portions of the second support element, the angles being measured prior to implantation. The angles are measured between the normals at the ends of the support elements. Preferably, the difference between (a) the angle between the end portions of the first support element and (b) the angle between the end portions of the second support element is at least about 20°, more preferably at least about 25°, especially at least about 30°. It can be appropriate for a support element which is to be implanted in the lumbar region of the spine to have a larger angle between its end portions compared with a support element which is intended for implantation in the thoracic or other region of the spine.

Preferably, the first support element is capable of recoverable deformation from its original undeformed configuration (from which it had previously been deformed) such that the angle between its ends changes through at least about 20°, more preferably at least about 25°, especially at least about 30°. Recoverable deformation is deformation that can be recovered substantially completely back to the undeformed configuration when applied stress is removed, or otherwise when allowed to recover (for example as a result of heating to allow a transformation to austenite phase).

Especially when the second support element is not formed from a material with shape memory properties, the recoverable deformation from its undeformed configuration will generally be less than that which is available in the first support element.

The first support element or the second support element or both will preferably be a rod, especially with a solid cross-section. A rod support element can be hollow along at least part of its length. One or more of the support elements can be a plate.

The cross-sectional area of each support element will often be approximately constant over at least most of the length of the support element, with the possibility that the cross-section might vary in at least one end region to facilitate connection directly or indirectly to a vertebra at the end or to an adjacent support element. The cross-sectional area of the first support element can be different from the cross-sectional area of the second support element. For example, the cross-sectional area of the first support element or of the second support element might be at least about 10 mm$^2$, preferably at least about 20 mm$^2$, more preferably at least about 30 mm$^2$, for example about 40 mm$^2$. The difference between the cross-sectional areas of the first and second support elements might be at least about 3 mm$^2$, preferably at least about 5 mm$^2$, more preferably at least about 10 mm$^2$.

The cross-sectional shapes of the first and second support elements might be the same or might be different. One or both of the elements might have a rounded cross-sectional shape, especially circular. It can be preferred for an element sometimes to be non-circular to enable it to fit securely in a fastener in such a way that it can transmit torque to the fastener. For example, the element can have at least one flat face. Polygonal (regular or irregular) shapes can be useful, for example with at least four faces, including square or rectangular or trapezoidal (when the element has four faces when viewed in cross-section), or with six or eight or more faces. An element which has a generally rounded cross-section might have a flat face.

The support elements are capable of being connected directly or indirectly to one another so that the kit provides a continuous support for a spinal column which extends continuously between the furthest apart ends of the furthest apart support elements. Fixation devices for connecting support elements of a kit for supporting a spinal column are known, for example as used in the ISOLA spinal support system which is manufactured and sold by DePuy Spine Inc. That system includes a connector for spinal support rods in a side-by-side arrangement which is known as a tandem rod connector, and a connector for spinal support rods in an end-to-end arrangement which is known as a closed dual rod connector (wedding band).

Preferably, at least one of the fixation devices includes (a) a first connection feature by which the device can be connected to the first support element (generally towards its end), and (b) a second connection feature by which the device can be connected to the second support element (generally towards its end). Suitable fixation devices for connecting support elements of a kit can connect the elements in an end-to-end arrangement in the manner of a butt joint. Suitable fixation devices for connecting support elements of a kit can connect the ends of the element in a side-by-side arrangement in the manner of a lap joint. Suitable fixation devices for connecting support elements can comprise a housing with respective bores for receiving the ends of the support elements. The bores can be axially aligned and communicate with one another when the support elements are to be connected in a butt joint arrangement. Particularly when the support elements are connected with their ends non-aligned, the effective length of the implanted kit can be adjusted by moving the end of one or other of the support elements relative to the housing.

Fixation devices which include a housing with at least one bore for a support element can include a locking part by which the support element can be locked into the housing. A particularly preferred locking part is a threaded fastener which is received in a threaded bore in the housing.

It can be preferred for at least one of the fixation devices to comprise a socket portion which is located at or towards one end of one of the support elements, into which the end of the other of the support elements can be inserted in order to fix the support elements to one another in an end-to-end arrangement. The said socket portion can be permanently attached to the support element on which it is located, for example by being machined or cast as one part with the support element, or by permanent fixing thereto, for example by welding. The provision of a permanently attached socket portion on one of the support elements can be preferred in the case of the second support element when it is formed from a material which does not exhibit shape memory properties.

A support element can have socket portions at each of two opposite ends.

A fixation device which includes connection features for the first and second support elements can include a third connection feature by which the device can be fixed to a vertebra. A connection feature for fixation to a vertebra can comprise a hook, or a bone screw which is arranged to extend through an opening in the housing. Connection features of this general type for fastening spinal support elements to a patient's spinal column are known.

A connection feature for fixation to a vertebra can include a lateral arm which extends across the vertebra from the side of the spinal process on which the support elements are located to the other side of the spinal process. The transverse arm can then be fastened to the vertebra by means of a hook or a bone screw.

The kit can include a fixation device which includes (a) a first connection feature by which the device can be connected to one of the first and second support elements, and (b) a second connection feature by which the device can be fixed to a vertebra.

A fixation device which includes a housing with a bore into which a support element can extend will generally be formed from a metal, as is known. Suitable metals include certain stainless steels, and titanium and its alloys.

A fixation device which includes a feature by which the device can be fixed to a vertebra will generally be formed from a metal, as is known. Suitable metals include certain stainless steels, and titanium and its alloys.

The kit of the invention can be used in dynamic spinal support systems, for example to provide support over thoracic, lumbar and sacral vertebrae respectively. A first support element can be used to provide support in the thoracic region which is formed from a material which does not exhibit shape memory properties. This can stabilise the spine in the thoracic region and promote fixation. A second support element can be used to provide support in the lumbar region, which is formed from a shape memory material which exhibits enhanced elastic properties. This can provide flexibility allowing the spine to flex in the lumbar region. A third support element can be used to provide support in the sacral region which is formed from a material which does not exhibit shape memory properties. This can stabilise the spine in the sacral region and promote fixation.

The kit of the invention can be used in the treatment of scoliosis. A first support element can be used to provide support in the lumbar region which is formed from a material which does not exhibit shape memory properties. This can stabilise the spine in the lumbar region and promote fixation. A second support element can be used to provide support in the thorocolumbar region, which is formed from a shape memory material which exhibits thermally initiated shape recovery properties. This can exert corrective forces on the spine over time. A third support element can be used to provide support in the upper thoracic region, which is formed from a shape memory material which exhibits enhanced elastic properties. This can provide flexibility allowing the spine to flex in the upper thoracic region.

The kit of the invention can be used in the treatment of trauma damage to the spine. A first support element can be used to provide support in the region of the spine which has been damaged, which is formed from a material which does not exhibit shape memory properties. This can stabilise the spine in the damaged region. Further support elements can be used to provide support in adjacent regions, which are formed from a shape memory material which exhibits enhanced elastic properties.

The kit of the invention can be used in the treatment of a spine which is affected by a degenerative disease. A first support element can be used to provide support in the diseased region, which is formed from a shape memory material which exhibits thermally initiated shape recovery properties. This can exert corrective forces on the spine over time. Further support elements can be used to provide support in adjacent regions, which are formed from a shape memory material which exhibits enhanced elastic properties.

Embodiments of the invention will now be described by way of example with reference to the accompanying drawings, in which.

Figure 1:
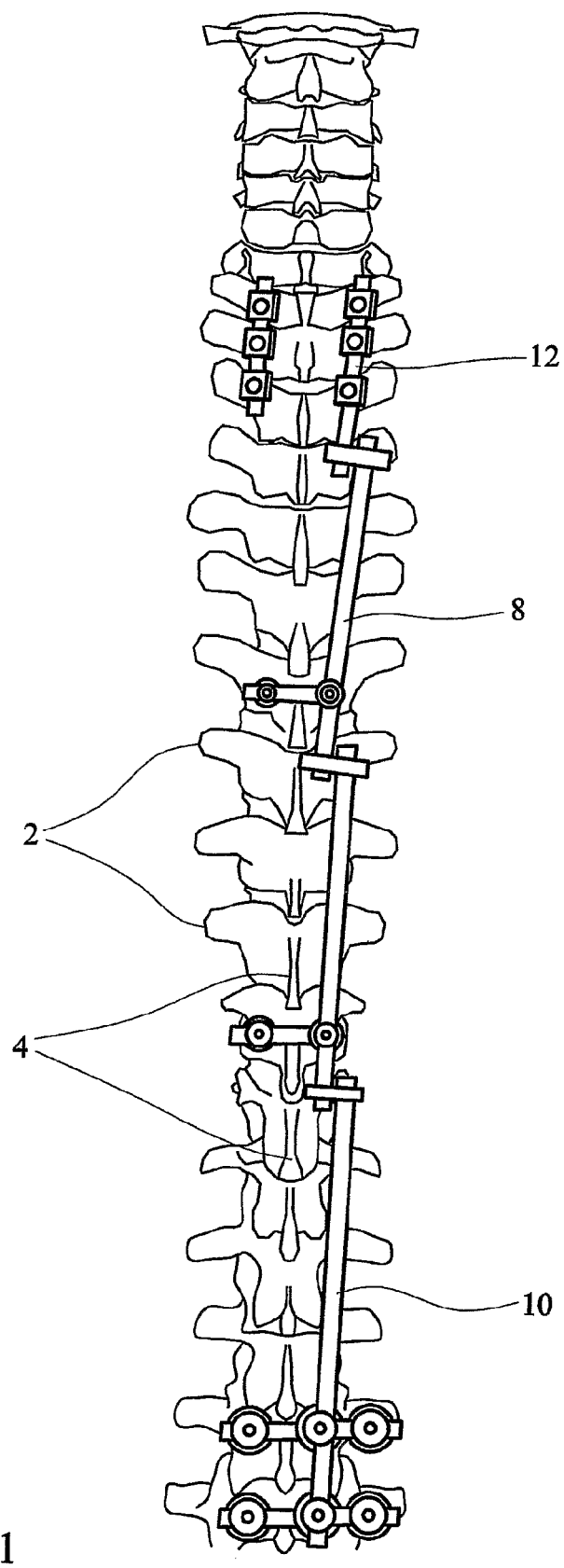
FIG. 1 shows a spinal column with spinal support elements of a spinal support kit according to the invention fastened to it by means of fixation devices.

Referring to the drawings, FIG. 1 shows a spinal column viewed posteriorly which comprises a plurality of vertebrae 2. The posteriorly extending spinal process 4 is visible. The present invention provides a kit which includes a plurality of spinal support elements 6, each in the form of a rod, which can support the spinal column and, in particular, apply forces to the vertebrae to correct deformities.

The kit comprises two support elements 8 which are intended for use in the thoracic region which are formed from a shape memory alloy which consists of 50.8 at-% nickel and the balance (apart from impurities) titanium. The alloy has been treated so that its $A_f$ temperature is about 20° C. This means that the alloy is able to exhibit superelastic properties, allowing it to be deformed in order to be fitted to the vertebrae. Once deformed (for example by as much as 8%), the element tends towards its configuration prior to deformation, applying forces to the vertebrae to which it is attached.

The kit further includes support elements 10 which are formed from titanium which are intended for use in the lumbar region.

The kit also includes support elements 12, also formed from titanium, which are intended for use in the cervical region.

Support elements which are formed from titanium have the advantage that they can be cut to a desired length more easily that is the case with support elements which are formed from a nickel-titanium based alloy.

The kit includes fixation devices by which the spinal support elements can be fastened to the patient's vertebrae. The support elements are fastened to the vertebrae by means of bone screws. Each bone screw passes through an aperture in the base of a channel member which is dimensioned to receive a spinal support element between the side walls of the channel member. The internal side walls of the channel member are threaded to engage the threads on the circumferential wall of a screw which can be located within the channel member to retain the support element therein. This approach to fixation of spinal support elements is known, for example from the implant system which is sold by DePuy Spine Inc under the trade mark EXPEDIUM.

Figure 2B:
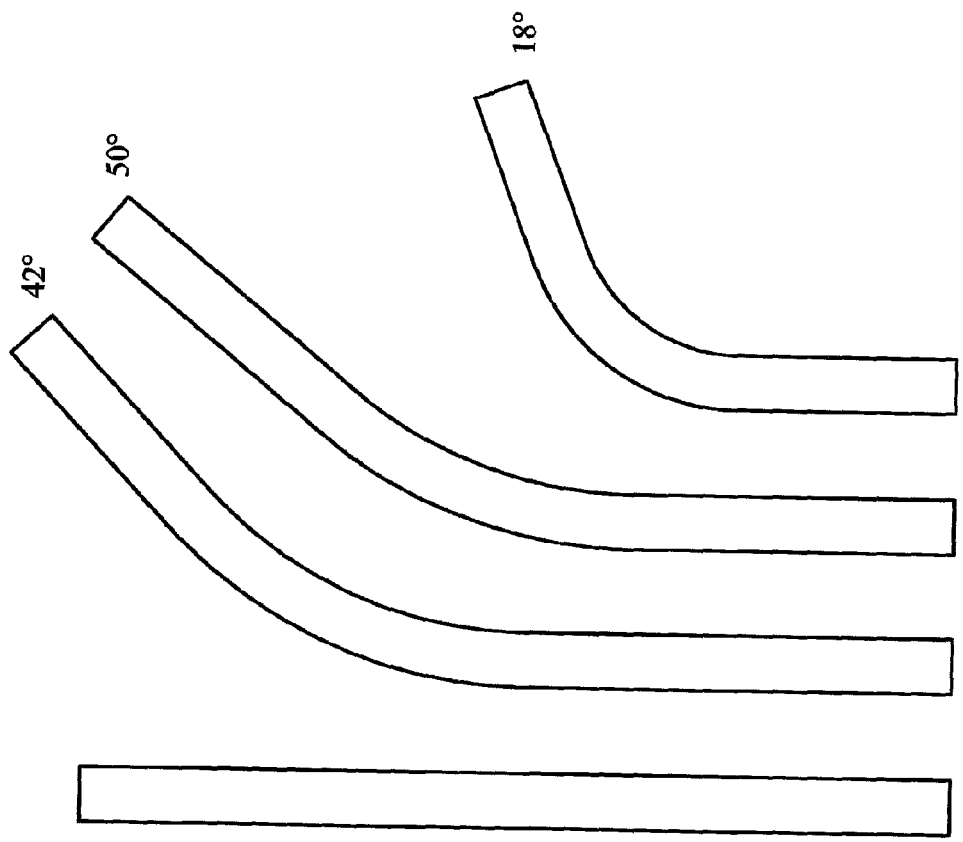
FIG. 2B illustrates side views of spinal support elements which can be used in the kit of the invention.
Figure 2A:
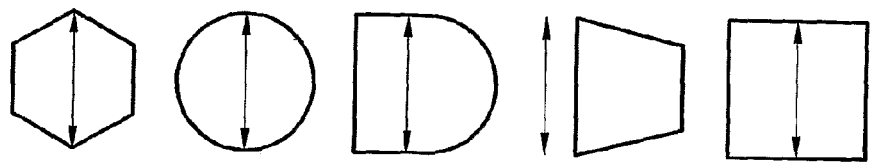
FIG. 2A illustrates end views of spinal support elements which can be used in the kit of the invention.

FIG. 2a shows cross-sections through spinal support elements which can be used in the kit of the invention. Suitable support elements can have shapes when viewed in cross-section which are hexagonal, circular, half-round (with a flat face), trapezoidal and square. The support elements will generally have the same cross-section from one end to the other end. However, it will often be appropriate for the cross-section to vary in at least some parts, especially at the ends of the rods. Reasons for changing the cross-section include ease of fixation in the fixation devices, and the desired degree to which torsional forces (when required) can be transmitted to fixation devices to which the support elements are attached.

Suitable cross-sectional areas for the support elements include about 12 mm², 20 mm², and 28 mm².

FIG. 2b shows schematically the range of shapes of support elements which might be used in the kit of the invention. Examples of useful lengths of the rods include 80 mm, 120 mm and 160 mm (or other lengths within and beyond this range). The support elements might be straight, or might define a Cobb angle of 18°, 42° or 50° (or other angles within and beyond this range).

Figure 3A:
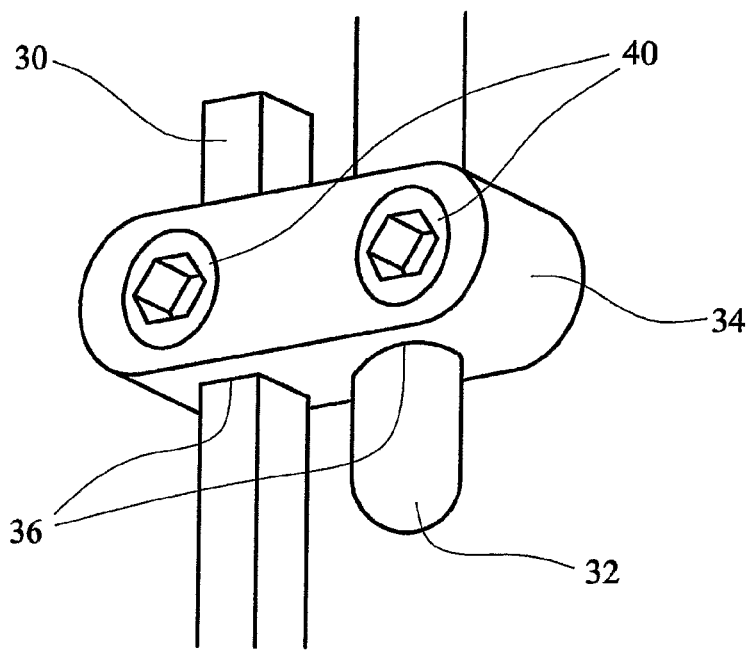
FIG. 3A is a perspective view of a fixation device for connecting a plurality of spinal support elements.

FIG. 3a shows a fixation device by which two support elements 30, 32 can be connected to one another side-by-side in a lap joint arrangement. In the illustrated embodiment, one of the support elements 30 has a square cross-section, at least at it end, and the other support element 32 has a round cross-section. The device comprises a housing 34 having two through bores 36 extending through it which are parallel. Each of the bores has a square cross-section so that the ends of the support elements are sliding fit therein.

The housing also has a pair of fixation bores formed in it extending generally perpendicular to the through bores 36. The fixation bores are threaded internally so that each of them can receive a fixation screw 40.

In use, the ends of the support elements are inserted into respective ones of the through bores, and moved relative to the through bores until they are positioned appropriately having regard to the desired overall length of the implant. Each of the fixation screws 40 is then tightened in the housing so that it acts on the inserted end of the respective support element.

Figure 3B:
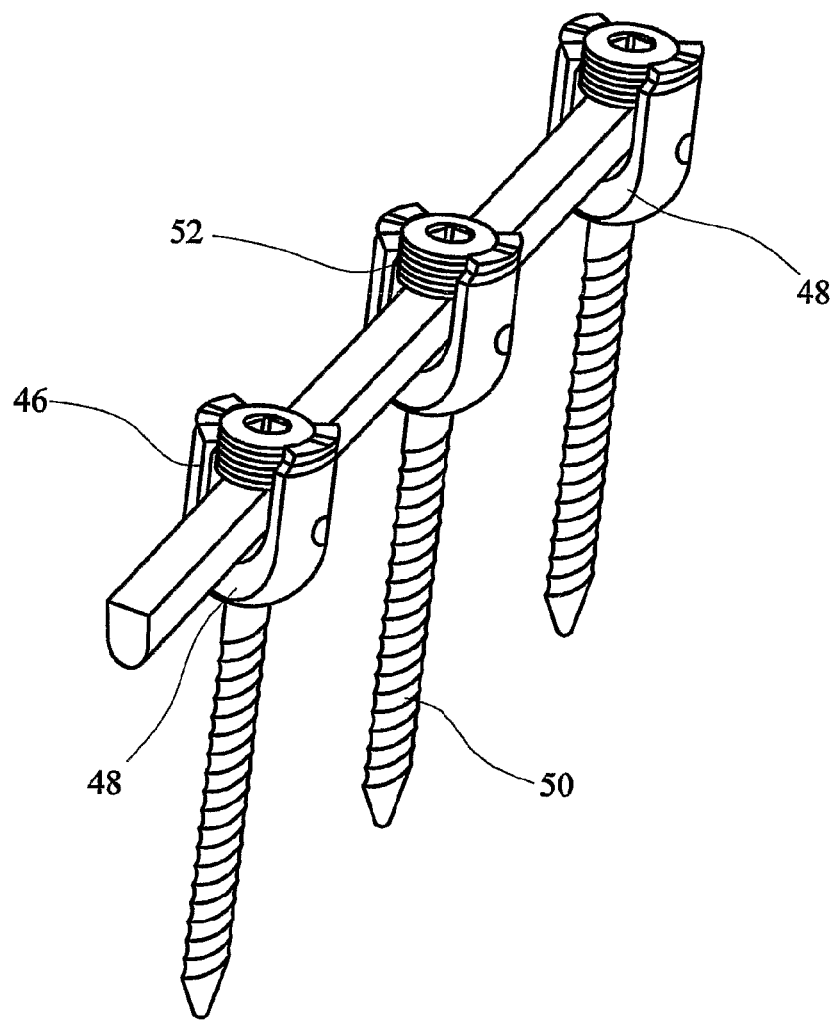
FIG. 3B is a perspective view of a plurality of fixation devices for connecting a spinal support element to bone.

FIG. 3b shows a fixation device of a commonly known type which can be used to fix a support element to bone tissue. The fixation device comprises a channel defined by side walls 46 and a base 48. A support element can be fitted into the channel between the side walls. The channel has a threaded shaft 50 extending from its base, which can be screwed into bone tissue. The configuration of the bone engaging thread is optimised as known.

The internal surfaces 52 of the side walls bear a thread, which can be engaged by a locking screw (not shown) to retain the support element in the channel, as known.

Figure 3C:
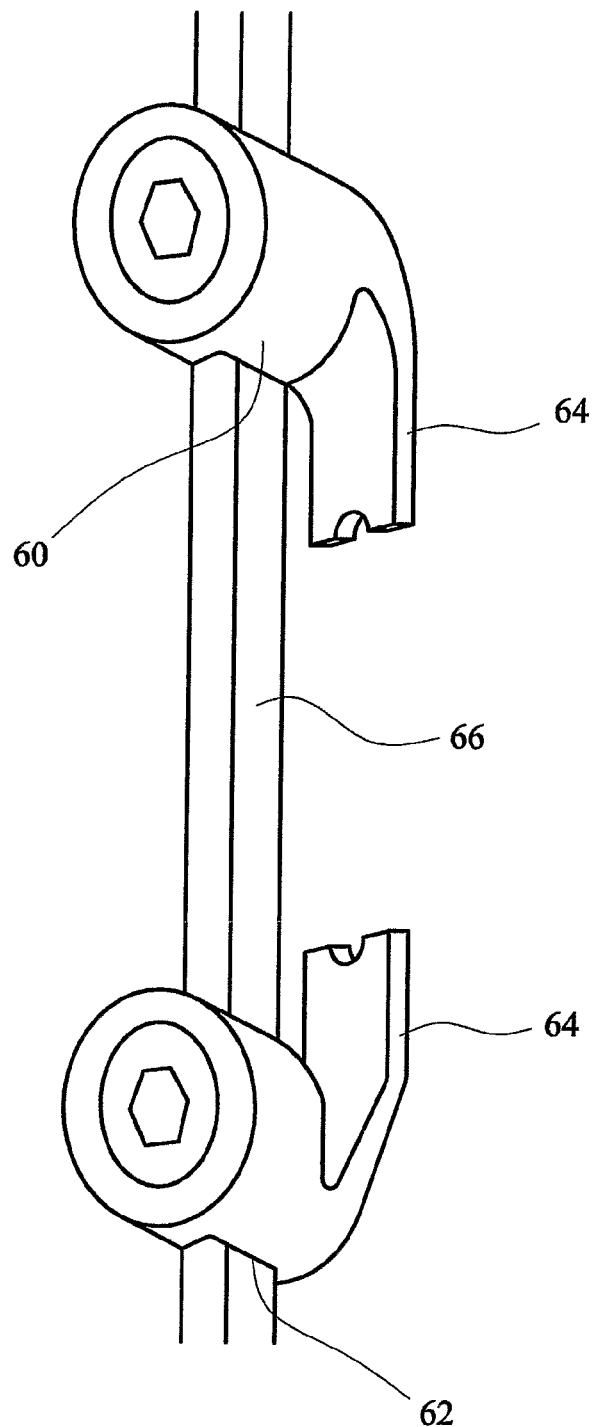
FIG. 3C is a perspective view of a plurality of fixation devices for connecting a spinal support element to bone.

FIG. 3c shows another fixation device of a commonly known type which can be used to fix a support element to bone tissue. The fixation device comprises a channel defined by side walls 60 and a base 62. A support element can be fitted into the channel between the side walls. The channel has a hook 64 on its base, which can engage bone tissue on a patient's vertebra, as known. A support rod 66 is located in the channel in the fixation device.

Examples of spinal support kits according to the invention are as follows:

EXAMPLE 1

Support Elements

| Spinal levels | Length (mm) | Cross-section shape | Cross-section dimensions (mm) | Material | $A_f$ temperature (° C.) | Tensile strength (MPa) |
|---|---|---|---|---|---|---|
| L5-L1 | 150 | □ | 6.0 | NiTi | 15 | 551 |
| T12-T4 | 200 | ⏢ | 5.0 | NiTi | 32 | 551 |

-continued

| Spinal levels | Length (mm) | Cross-section shape | Cross-section dimensions (mm) | Material | $A_f$ temperature (° C.) | Tensile strength (MPa) |
|---|---|---|---|---|---|---|
| T3-C6 | 80 | | 3.5 | Ti | — | 860 |

Fixation Elements

| Spinal levels | Fixation elements |
|---|---|
| L5-L1 | Pedicle screws |
| T12-T4 | Pedicle screws |
| T3-C6 | Hooks |

EXAMPLE 2

Support Elements

| Spinal levels | Length (mm) | Cross-section shape | Cross-section dimensions (mm) | Material | $A_f$ temperature (° C.) | Tensile strength (MPa) |
|---|---|---|---|---|---|---|
| L3-L1 | 100 | | 6.0 | Ti | — | 860 |
| T12-T4 | 200 | | 4.5 | NiTi | 32 | 551 |
| T3-T1 | 80 | | 3.5 | Ti | — | 860 |

Fixation Elements

| Spinal levels | Fixation elements |
|---|---|
| L3-L1 | Pedicle screws |
| T12-T4 | Hooks |
| T3-T1 | Pedicle screws |

The invention claimed is:

1. An implant kit for supporting a spinal column, which comprises:
   a. at least first and second support elements for fixation to vertebrae of a spinal column, extending generally along the spinal column between spaced apart vertebrae,
   b. a plurality of fixation devices for (i) fixing the support elements to one another in an end-to-end arrangement and (ii) fixing the support elements to the vertebrae,
wherein the material of the first support element is different from the material of the second support element, and the first support element is formed from a metal which exhibits thermally initiated shape memory properties and the second support element is formed from a metal which does not exhibit thermally initiated shape memory properties, the metal of the first support element having an $A_f$ temperature between about 20° C. and about 32° C. such that the metal of the first support element may be cooled to a martensitic state, bent to conform to the spinal column in a pre-corrected state, and heated to an austenitic state to apply a corrective force to the spinal column.

2. A kit as claimed in claim 1, in which the first support element is longer than the second support element.

3. A kit as claimed in claim 1, in which the angle between the end portions of the first support element is greater than the angle between the end portions of the second support element, the angles being measured prior to implantation.

4. A kit as claimed in claim 3, in which the difference between (a) the angle between the end portions of the first support element and (b) the angle between the end portions of the second support element is at least about 20°.

5. A kit as claimed in claim 1, in which at least one of the fixation devices includes (a) a first connection feature by which the device can be connected to the first support element, and (b) a second connection feature by which the device can be connected to the second support element.

6. A kit as claimed in claim 5, in which the said fixation device includes a third connection feature by which the device can be fixed to a vertebra.

7. A kit as claimed in claim 1, in which at least one of the fixation devices comprises a socket portion which is located at or towards one end of one of the support elements, into which the end of the other of the support elements can be inserted in order to fix the support elements to one another in an end-to-end arrangement.

8. A kit as claimed in claim 7, in which the said socket portion is permanently attached to the support element on which it is located.

9. A kit as claimed in claim 1, in which at least one of the fixation devices includes (a) a first connection feature by which the device can be connected to one of the first and second support elements, and (b) a second connection feature by which the device can be fixed to a vertebra.

10. A kit as claimed in claim 1, in which the shape of the first support element when viewed in cross section is different from the shape of the second support element when viewed in cross-section.

11. A kit as claimed in claim 1, in which the cross-section of at least one of the first and second support elements is non-round.

12. A kit as claimed in claim 1, in which the first support element is formed from a nickel-titanium based alloy.

13. An implant kit for supporting a spinal column, which comprises:
   at least first and second spinal rods for fixation to vertebrae of a spinal column, extending generally along the spinal column between spaced apart vertebrae,
   a plurality of bone anchors for fixing the spinal rods to the vertebrae and a plurality of spinal rod connectors for fixing the spinal rods to one another, the plurality of bone anchors including a plurality of bone screws each having a proximal channel for receiving one of the spinal rods and a distal threaded shaft for screwing into the vertebra, the plurality of spinal rod connectors including one or more tandem rod connectors permitting the connection of two spinal rods in an side-by-side relationship,
   wherein the material of the first spinal rod is different from the material of the second spinal rod, and the first spinal rod is formed from a metal which exhibits thermally initiated shape memory properties and the second spinal rod is formed from a metal which does not exhibit thermally initiated shape memory properties, the metal of the first spinal rod having an $A_f$ temperature between about 20° C. and about 32° C. such that the metal of the first spinal rod may be cooled to a martensitic state, bended to conform to the spinal column in a pre-corrected state, and heated to an austenitic state to apply a corrective force to the spinal column through the bone anchors.

14. A kit as claimed in claim 13, wherein the plurality of bone anchors further comprises a plurality of bone hooks having a proximal channel for receiving of the spinal rods and a distal hook for engaging one of the vertebra.

15. A kit as claimed in claim 13, wherein the first spinal rod has a first cross section and the second spinal rod has a second cross section distinct from the first cross section.

16. A kit as claimed in claim 15, wherein the plurality of bone screws includes a set of bone screws having a channel corresponding to the first cross section of the first spinal rod and a set of bone anchors having a channel corresponding to the second cross section of the second spinal rod.

17. A kit as claimed in claim 16, wherein at least one of the tandem rod connectors includes a housing having two parallel bores therethrough, one of the bores having a cross-sectional shape corresponding to the first cross section of the first spinal rod and the other bore having a cross section corresponding to the second cross section of the second spinal rod.

18. A kit as claimed in claim 17, wherein the first cross section includes two opposed planar side surfaces and the second cross section is circular.

19. A kit as claimed in claim 18, wherein the first cross section is rectilinear.

20. A kit as claimed in claim 18, wherein the first cross section is trapezoidal.

* * * * *